United States Patent [19]
Chiang et al.

[11] Patent Number: 5,660,183
[45] Date of Patent: Aug. 26, 1997

[54] INTERACTIVE PROBABILITY BASED EXPERT SYSTEM FOR DIAGNOSIS OF PACEMAKER RELATED CARDIAC PROBLEMS

[75] Inventors: Chih-Ming J. Chiang, Highlands Ranch, Colo.; Alan D. Bernstein, Montvale; Victor Parsonnet, Millburn, both of N.J.; Tibor Nappholz, Englewood, Colo.

[73] Assignee: Telectronics Pacing Systems, Inc., Englewood, Colo.

[21] Appl. No.: 515,996

[22] Filed: Aug. 16, 1995

[51] Int. Cl.$^6$ ........................ A61B 5/00
[52] U.S. Cl. ...................... 128/695 R; 128/702
[58] Field of Search ............. 607/27, 30; 128/695, 128/702; 364/413.06, 413.02

[56] References Cited

U.S. PATENT DOCUMENTS

| | | | |
|---|---|---|---|
| 4,730,259 | 3/1988 | Gallant | 364/413.02 |
| 4,825,869 | 5/1989 | Sasmor et al. | 128/419 |
| 4,872,122 | 10/1989 | Altschuler et al. | 364/413.02 |
| 5,265,010 | 11/1993 | Evans-Paganelli et al. | 364/413.02 |
| 5,276,612 | 1/1994 | Selker | 364/413.06 |
| 5,277,188 | 1/1994 | Selker | 128/695 |
| 5,357,976 | 10/1994 | Feng | 128/731 |

OTHER PUBLICATIONS

Expert System and Diagram for Troubleshooting Dual Chamber Pacemakers, Walter H. Olson, Michael V. McConnell, Robert L. Sah, Peter I. Hong; 1985 IEEE, pp. 53–58.
Calvin: An Expert System to Improve Arrhythmia Detector Performance in Noise, Roger G. Mark, Ramesh Patil, and George Moody; Journal of Electrocardiology, Supplemental Issue 1988, p. S117.
NASPE Abstracts, Apr. 1992, Part II, PACE, vol. 15, p. 510.

*Primary Examiner*—William E. Kamm
*Assistant Examiner*—George R. Evanisko
*Attorney, Agent, or Firm*—Gottlieb, Rackman & Reisman

[57] ABSTRACT

A diagnostic device for providing a prognosis of patient with an implanted cardiac device includes a data bank for storing statistical data relating various symptoms characterizing cardiac problems and associated complications. The device further includes an input device so that a clinician can enter patient specific data including his symptoms. A set of rules stored in a memory are used to provide a diagnosis for the patient based on the statistical data. Preferably the diagnostic device is incorporated in a programmer for a pacemaker or other implantable cardiac device.

11 Claims, 2 Drawing Sheets

INTERACTIVE PROBABILITY BASED EXPERT SYSTEM FOR DIAGNOSIS OF PACEMAKER RELATED CARDIAC PROBLEMS

BACKGROUND OF THE INVENTION

A. Field of Invention

This invention pertains to a system and method of providing diagnosis for cardiac problems of a patient based on a statistical data base, said problems being generally related to the operation of an implantable cardiac device (ICD) for said patient. The term ICD, or pacemaker is used interchangeably herein to designate pacemakers as well as implantable defibrillators and similar devices used for brady-or tachycardiac therapy and/or defibrillation.

B. Description of the Prior Art

Cardiac pacemakers have become complex over the recent years, with more and more features, such as modes of operations, lead choices, adaptive rate pacing, and mode switching for atrial tachycardias. As a result, typical dual chamber, dual sensor pacemakers presently in use are very complex, requiring more than 40 programmable parameters to be set (either automatically or by a physician) prior to operation. If a pacemaker is not programmed optimally for a patient's condition, and/or the patient's condition changes over time, a fairly natural occurrence, it is often difficult to diagnose the resulting symptoms as either pathological, or due to inappropriate pacemaker operation. Additionally, component failure, while extremely rare, may also result in patient symptoms which are difficult to diagnose. Thus the task of diagnosing problems of patients with pacemakers, whether pacemaker related or pathological, is difficult, requiring extensive specialized training and adds to the cost of providing pacemakers and health care to the patient.

Several solutions have been attempted in the past, in which an expert system was utilized to diagnose cardiac problems. The most common approach n these systems was to automatically interpret electrocardiograms. See Olson, W. H., McConnell, M. V., Sah R. L. *Expert System and Diagram for Troubleshooting Dual Chamber Pacemakers*, Computers in Cardiology, IEEE Computer Society Press, 1985:53–58; Mark, R. G., Patil, R., Moody,G. *An Expert System to Improve Arrythmia Detector Performance in Noise*, Journal of Cardiology, 1988 Supplement, S117; U.S. Pat. No. 4,825,869 to Sasmor. However, this approach does not take into consideration patient symptoms, which, in the inventors opinions, provide important diagnostic clues which may help solve the problem being addressed. For example, the Olson reference uses electrocardiograms with pacemaker generated timing diagrams for indicating atrial and ventricular timing problems. However this system may be used only with a dedicated pacemaker having the capability to generate the aforementioned timing diagrams. Moreover, the system is unable to diagnose common problem such as loss of capture, under-sensing and over-sensing of cardiac activity.

The Sasmor reference provides an overall diagnostic scheme making use of physiological signals such as atrial and ventricular intracardiac electrograms, surface electrocardiograms and timing diagrams, event interpretation. However, this system also fails to take into consideration patient symptoms and rules are heuristic and ad hoc, reflecting a particular clinician's bias.

Therefore, generally, most prior systems incorporate merely electrocardiograms interpretation schemes and not a complete diagnosis and fail to take avail themselves of patient symptoms.

OBJECTIVES AND ADVANTAGES OF THE PRESENT INVENTION

In view of the above-mentioned disadvantages of the prior art, it is an objective of the present invention to provide an expert system containing statistical data related to cardiac problems and pacemaker/electrode or other cardiac etiologies which are associated with these problems instead of ad hoc heuristics.

A further objective is to provide an expert system with means for developing rules based on said data, said rules being used to provide diagnosis for a patient responsive to the patient's symptoms and other information.

A further objective is to provide a system which is flexible so that it can adapt automatically to new data, and to generate new rules based on said data.

A further objective is to provide an expert system which can be incorporated into a pacemaker programmer to result in a fast and accurate analysis of a pacemaker operation during follow-up visits.

Yet another objective is to provide a device which may be used as a teaching tool for a physician to learn about various cause/effect relationships affecting cardiac patients.

A further objective is to provide a device which is user friendly and easy to use.

Yet another objective is to provide a device which is interactive and is not strictly clinician-oriented, nor is it completely automatic. Purely automatic diagnostic devices are disadvantageous in that it cannot accommodate patient symptoms or clinical observations. Purely clinical systems are undesirable because they are prone to human errors and are time consuming.

Other objectives and advantages of the invention shall become apparent from the following description. Briefly, an expert system constructed in accordance with this invention consists of memory means used to store a set of rules, and, optionally, an extensive data base descriptive of statistical data obtained over extended time period about cardiac patients, including various problems, or complication suffered by the patients, and symptoms associated with each complication. The system further includes means for generating said rules from the data base, using, for example, well known statistical analyses tools such as Bayes theorem. Although the system may be provided as an independent unit, it is expected that typically, the system is incorporated into a pacemaker programmer.

When a patient goes for a visit and complains of a problem, the clinician collects the patient specific information and accesses the diagnostic system if the patient complains of a problem or if the clinician observes something wrong. In response to prompts from the system, the physician enters symptoms he observes, and/or are reported by the patient. The system incorporates a pre-setable probability threshold indicative of the confidence level of the diagnosis. Based on the symptoms, the system generates either a positive diagnosis for the problem, based on the rules developed as set forth above, or if none of the probable causes related to the particular problem has a sufficiently high probability to become a positive prognosis, then a list of probable causes is generated. Optionally, the system further generates a list of additional symptoms frequently associated with the most likely problem so far and provides advice as to possible action that may be taken to alleviate or eliminate the problem.

Over time, new data developed associating problems with symptoms, and this data is also fed into the system and used to update and maintain the current data base. At regular intervals, or on demand, the rules are recalculated to incorporate the new data.

DETAILED DESCRIPTION OF THE INVENTION

Figure 1:
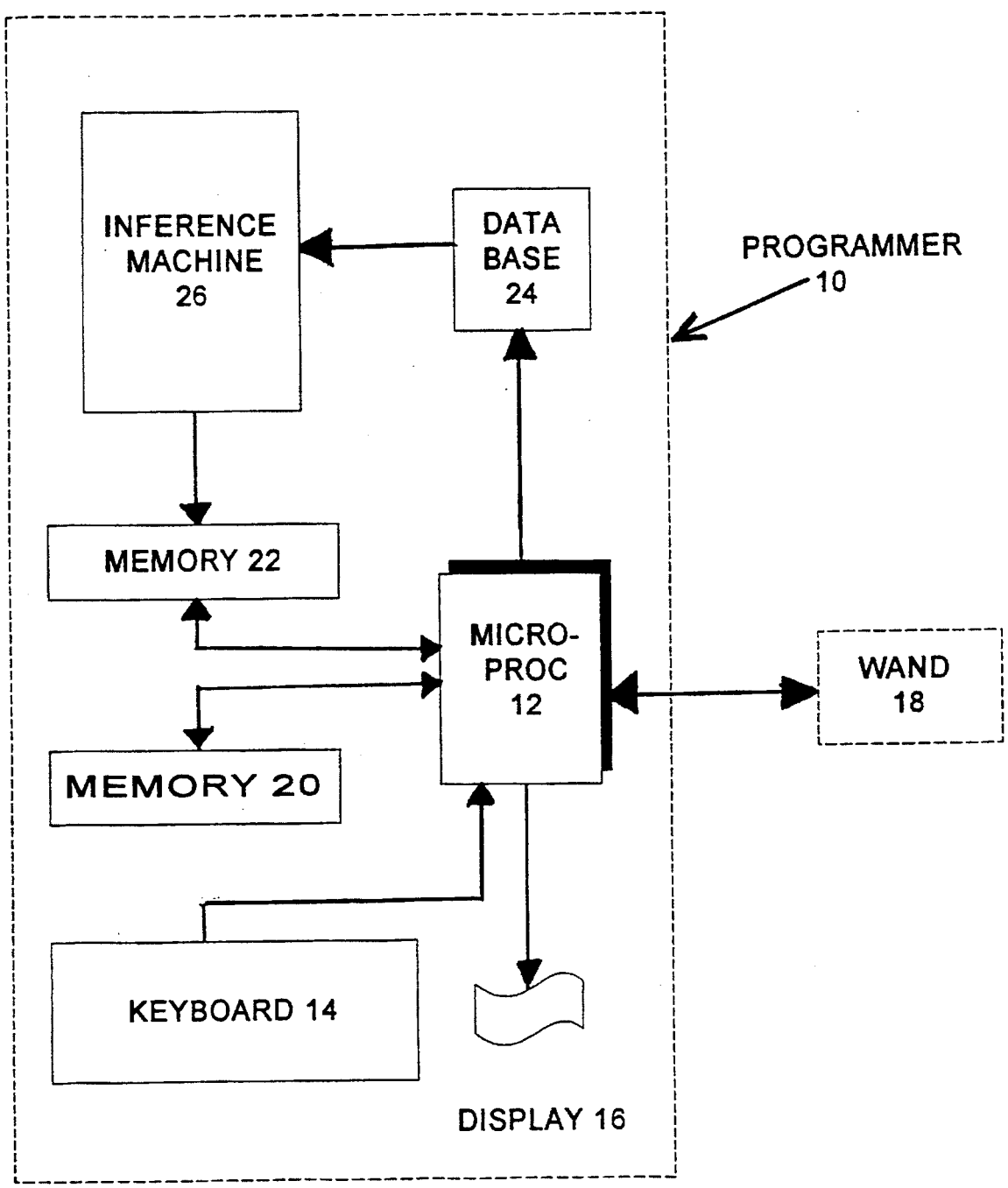
FIG. 1 shows a block diagram of a programmer incorporating an expert system constructed in accordance with this invention.

FIG. 1 shows an apparatus for diagnosing a cardiac patient, said apparatus being incorporated into a pacemaker programmer 10. The programmer 10 includes a microprocessor 12 communicating with a keypad 14, a display 16, and a programming wand 18. The programmer 10 is constructed and arranged to initiate and to change the programming of an implanted pacemaker or other implanted cardiac device (not shown) used to provide therapy to the patient through wand 18. Various programs for this purpose as well as associated data is stored in a first memory 20. These programmers are available, for example, from Telectronics Pacing Systems, Inc. of Englewood Colo., as the series 9600 and 9602 Network Programmer.

Importantly, the programmer 10 is modified to further includes a second memory 22 containing a set of diagnostic rules. These diagnostic rules are used by the programmer to provide to the physician a prognosis of the patient based on the symptoms noted by the physician as well as data collected by the programmer from the patient. Details of this operation are set forth in the flow chart of FIG. 2. In step 100, the physician initiates a diagnostic subroutine. This step may be performed, for example, by providing a menu for the physician on display 16, and prompting the physician to chose a particular key of keypad 14.

Memory 20 is used to store various patient specific information which has been either entered by the physician earlier for the initialization or other functions associated with the pacemaker, or has been downloaded or otherwise derived from the pacemaker itself. This information may include the patient's age, sex, physical condition, lead impedance, sensing and pacing threshold levels, histograms of recent cardiac episodes, indications for pacing, pacemaker manufacturer, date of pacemaker and lead implantation, lead type, current programming parameters etc. by the microprocessor 12. This information is retrieved in step 102.

Next, in step 104, the physician enters various symptoms or complications associated with the patient. Again, this may be accomplished by listing on display 16 a plurality of various symptoms normally associated with cardiac patients, and then prompting the physicians to select the symptoms which are applicable to the patient from the displayed list. Some of these symptoms and the associated etiologies are listed below.

| SYMPTOMS-$Co_i$ | ETIOLOGIES-$Ca_j$ | PROBABILITY $P(Ca_i|Co_j)$ |
| --- | --- | --- |
| Atrial Flutter | Underlying Rhythm Change | 0.77 |
| " | Inappropriate Mode Programming | 0.16 |

-continued

| SYMPTOMS-$Co_i$ | ETIOLOGIES-$Ca_j$ | PROBABILITY $P(Ca_i|Co_j)$ |
| --- | --- | --- |
| Shortness of Breath | Inappropriate Mode Programming | 0.16 |
| " | Inappropriate Mode Programming | 0.14 |
| " | Inappropriate Rate Response Parameter Programming | 0.11 |
| " | Underlying Rhythm Change | 0.11 |
| " | Inappropriate Maximum Tracking Rate Programming | 0.05 |
| Pace Failure No Stimuli | Conductor Fracture | 0.30 |
| " | Pulse generator Failure | 0.11 |
| " | Oversensing | 0.13 |
| " | Back-up Mode | 0.09 |
| " | Back-up Mode | 0.09 |
| " | Battery Depletion | 0.07 |

In step 106 the microprocessor 12 accesses the diagnostic rules stored in memory 22 related to the data obtained in steps 102 and 104. These rules may be expressed for example as a set of 'If O then B' statements where O is a particular symptom, and B is a possible etiology for symptom O. Associated with each statement there is also a statistical probability value $P(Co|Ca)$ indicative for that statement. A set of symptoms, $Co_i$, and a plurality of etiologies, $Ca_j$ associated with each symptom $Co_i$, and the corresponding probabilities $P(Ca_j|Co_j)$ are shown in the following table. The data from this table was developed using information derived from a number of patients having a total of 2093 problems over some nine years.

This data may be stored in memory 22 in the form of look-up table, as a spread sheet data or in other formats.

In step 106, the microprocessor 102 retrieves all the entries for the particular symptoms selected by the physician.

In step 108 the number of symptoms selected is checked. If only a single symptom has been selected than in step 110 all the potential causes which could have resulted in that one symptom are ordered by their probability $P(Ca|Co)$. In the following step 112 a check is performed to determine if highest $P(Ca|Co)$ is larger than a preselected threshold value K. Preferably K is in the range of 60% to 80% and may be preset by the physician. This check provides a measure of confidence in the prognosis derived by the system. If this probability exceeds the constant K, then in step 116, the microprocessor 12 shows on display a message identifying the most probable cause leading to the selected symptom. In addition, in step 116 a message is displayed of possible therapy.

If in step 112 the largest probability is smaller than constant K, then in step 118 a message is displayed indicating that there was insufficient information to make a conclusive prognosis. Optionally, in step 120 the cause having the highest probability is displayed followed by the additional causes which may have led to the be associated from the symptom. It also lists other confirming symptoms with the most likely cause. This approach at least provides the physicians with some indication as to what other symptoms should be investigated.

If in step 108 it is determined that several symptoms have been selected then in step 122 measuring values are calculated for each cause and associated N symptom, using the formula:

$$M[Ca|Co_{1,2\ldots N}] = M[Ca_i|Co_{1,2\ldots N-1}] + (1-M[Ca_i|Co_{1,2,\ldots N-1}])*P[Ca_i|Co_N]$$

As more and more complications are analyzed and installed into the data base the probabilities of a cause increases to 100%. For two symptoms, $$M[Ca_i|Co_{j,k}] = P[Ca_i|Co_j] + (1-P(Ca_i|Co_j))*P[Ca_i|Co_k]$$

This expression is calculated for each two symptoms and used to calculate the generalized measure M. This number is then used instead of probability P in steps 112–120.

Figure 2:
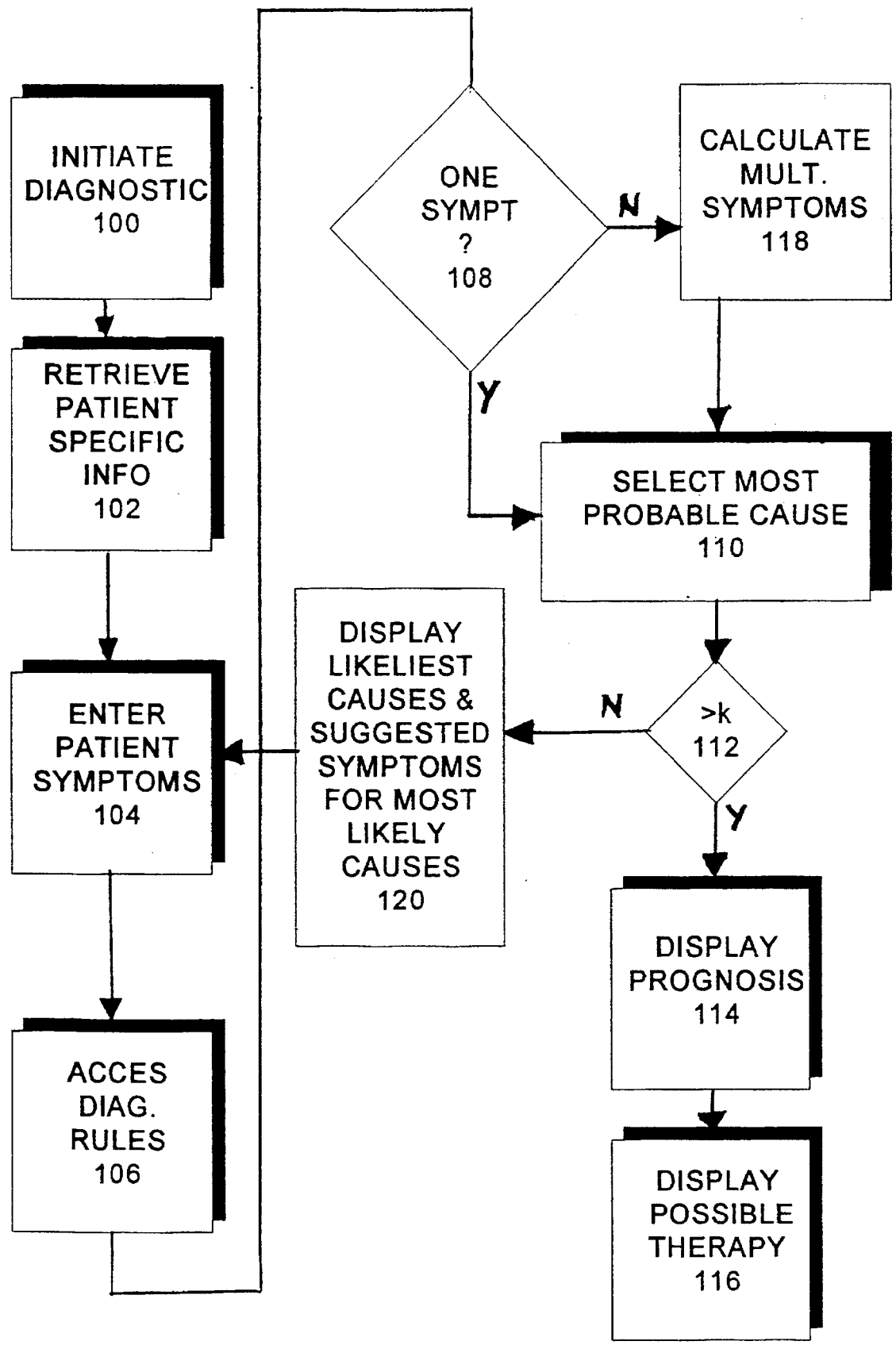
FIG. 2 shows a flow chart of the subject system.

Of course, before the system can work, the rules stored in memory 22 and utilized by the flow chart of FIG. 2 must be generated. For this purpose, first a large amount of data is collected, correlated and analyzed. Much of this data is available for clinical studies. See Parsonnet, V; Neglia, D; Bernstein, A. D. *The frequency of pacemaker-system problems, etiologies and corrective interventions;* PACE 1992; 15:510; Dyszliewicz W.; Sarnowski, W. Zerbe,F. Et al *Early complications after pacemaker implantation: A review of* 1080 *cases;* PACE 1993;16:1138. Statistical data is derived from this raw information defining a plurality of probabilities(Co|Ca$_i$), i.e., the probability that a symptom or complication Co has been caused by an etiology Ca$_i$ where is index assigned to each etiology resulting in symptom Co. In addition, a probability P ( Ca$_i$ ) for each etiology Ca$_i$ is also tabulated from the database. After these probabilities have been calculated, the posteriori probabilities P(Ca$_i$|Co) is readily calculated from the Bayes Theorem. More particularly, the probability that a particular symptom has been caused by an etiology Ca$_i$ is given by :

$$P(Ca_i|Co) = [P(Co|Ca_i)* P(Ca_i)]/\Sigma[P(Co|Ca_i)* P(Ca_i)]$$

Where N is the total number of etiologies which can cause the symptom Co. The rules thus calculated can be derived either in the programmer, or externally by a general purpose computer and then fed to the memory 22.

An important feature of the invention is that the programmer 10 can be provided with its own data base 24 and an inference machine 26. The data base 24 includes statistical data collected by others as well as data collected locally by a particular physician or group of physicians using a particular programmer. At regular intervals, for example, once a month, or on a continuous basis, the inference machine 26 is used to review the data in the data base and update the rule 22 in accordance with the expressions described above. The data base may also be updated on regular basis by adding additional information derived by third parties, such as clinical studies done at a university or other research facility. In this manner, the rules in memory 22 are continuously updated and refined, thereby insuring that the diagnostic expert portion of the programmer 10 is current.

The subject invention has a number of advantages over the prior art discussed above.

(1) The diagnostic expert system is using an expandable data base and therefore has learning capabilities. Every new diagnostic case is entered into the data base to update the rules used by the expert system. Thus the system is continuously improving itself.

(2) The statistical data used to generate the rules is derived from actual raw data obtained by clinicians rather than by making heuristic rules for diagnostics. A simple example is when a diagnosis is confirmed. The system automatically updates the relationships of all the observations to the confirmed diagnosis.

(3) The invention can handle uncertainty in symptoms and multiple observations of seemingly unrelated symptoms.

(4) The diagnostic system is universal in the sense that it can be applied to all pacemakers, independently of pacemaker manufacturer or model number, and can operate on a large number of different sources, including patient symptoms, patient specific information, telemetry data, statistical information based on other patients, ECG strips and so on.

(5) The subject invention is based on an algorithm which is neither wholly automated nor is strictly oriented to a specific clinicians. Therefore personal inclinations or bias by clinicians are eliminated.

(6) Finally, the invention provides an important learning tool for the physician since it clearly illustrates to the physician the relationships between various causes and effects associated with pacemakers and cardiac functions.

The principles of the invention have been described for a pacemaker however, as previously mentioned, they are also applicable to other implantable cardiac devices.

In the embodiment described herein, the various cause/effect relationships are classified by statistical probability. Other techniques may also be available to achieve the same results. One such technique would be to use fuzzy logic circuitry wherein the various cause/effect relationships and fuzzy logic rules are used to select the most appropriate pair.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. A cardiac diagnostic apparatus for diagnosing a patient comprising:

memory means for storing a set of rules, each rule defining a predetermined relation for each of a plurality of cardiac symptoms of patients with a corresponding etiology and a statistical probability relating each of said cardiac symptom to one of said corresponding etiologies;

means for receiving data descriptive of a patient's specific cardiac symptoms;

means for identifying rules from said set which are related to said specific cardiac symptoms;

means for automatically generating a prognosis for said specific cardiac symptoms based on said statistical probabilities, said prognosis identifying at least one etiology having a preselected statistical probability; and means for displaying said prognosis.

2. The apparatus of claim 1 wherein said memory means includes means for storing a plurality of suggested therapies, means for selecting one of said suggested therapies in association with said prognosis and means for displaying said one suggested therapy.

3. A programmer for programming a cardiac implant device, said programmer comprising:

first memory means for storing information related to programming operational parameters of a cardiac implant device;

second memory means for storing a set of diagnostic rules relating a predetermined plurality of cardiac symptoms of cardiac patients with corresponding etiologies, each rule defining a predetermined relation for each of a plurality of cardiac symptoms of patients with a corresponding etiology and a statistical probability relating each of said cardiac symptom to one of said corresponding etiologies;

data input means for inputting patient specific data into said programmer, including at least one cardiac symptom;

data communication means for exchanging data with a cardiac implant device, said data including programming data from and to said first memory means for programming said cardiac implant device;

processing means for processing the patient specific data and for automatically generating a prognosis based on at least said one cardiac symptoms and said rules to generate a prognosis, said prognosis identifying at least one etiology based on said at least one symptom and the related statistical probability; and output means for generating an output indicative of said prognosis.

4. The programmer of claim 3 wherein said data processing means identifies a plurality of applicable rules, each rule including said one symptom, and analyzes the probability of each applicable rule to generate said prognosis.

5. The programmer of claim 3 wherein said output means includes display means for displaying said prognosis.

6. The programmer of claim 3 further comprising third memory means for storing a statistical data base and an inference machine for deriving said rules from said data base.

7. The programmer of claim 6 wherein said processing means includes means for updating said data base by adding to said data base information received from new patients.

8. The programmer of claim 3 wherein said processing means includes comparing means for comparing the probability associated with a rule to a preset level, wherein said prognosis is generated if said probability exceeds said preset level.

9. The programmer of claim 8 wherein said preset level is programmable by said programmer.

10. A method of generating a prognosis for a patient having cardiac symptoms, comprising the steps:

providing a set of rules relating each cardiac symptom with a corresponding cardiac etiology, each rule being characterized by a corresponding probability derived from predetermined statistical information;

receiving at least one symptom specific to a particular patient;

identifying particular rules of said set related with said one symptom;

analyzing the probabilities associated with said particular rules; and generating a prognosis based on said analysis to define an etiology causing said one symptom.

11. The method of claim 10 wherein said receiving step includes receiving several symptoms, and wherein during said analysis each rule associated with each symptom is analyzed.

* * * * *